(12) United States Patent
Shin et al.

(10) Patent No.: US 9,433,655 B2
(45) Date of Patent: Sep. 6, 2016

(54) COMPOSITION COMPRISING NATURAL SUBSTANCE EXTRACT AS ACTIVE INGREDIENT FOR PREVENTING OR TREATING ACUTE RENAL FAILURE

(71) Applicant: KOREA INSTITUTE OF ORIENTAL MEDICINE, Daejeon (KR)

(72) Inventors: Hyun Kyoo Shin, Daejeon (KR); Ju Young Jung, Daejeon (KR); Hye Kyung Ha, Seoul (KR); Chang Seob Seo, Daejeon (KR); Young Jung Kim, Gwangju (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 14/441,172

(22) PCT Filed: Nov. 6, 2013

(86) PCT No.: PCT/KR2013/010017
§ 371 (c)(1),
(2) Date: May 6, 2015

(87) PCT Pub. No.: WO2014/073854
PCT Pub. Date: May 15, 2014

(65) Prior Publication Data
US 2015/0283195 A1    Oct. 8, 2015

(30) Foreign Application Priority Data

Nov. 8, 2012  (KR) .......................... 10-2012-0126354

(51) Int. Cl.
*A61K 36/00* (2006.01)
*A61K 36/53* (2006.01)

(52) U.S. Cl.
CPC ..................................... *A61K 36/53* (2013.01)

(58) Field of Classification Search
None
See application file for complete search history.

(56) References Cited

FOREIGN PATENT DOCUMENTS

| KR | 10-0857691 | 9/2008 |
|---|---|---|
| KR | 10-2009-0062342 | 6/2009 |
| KR | 10-2011-0036317 | 4/2011 |
| KR | 10-2012-0032405 | 4/2012 |

OTHER PUBLICATIONS

El-Sayed et al., "Hesperidin, an antioxidant flavonoid, prevents acrylonitrile-induced oxidative stress in rat brain", *J Biochem Molecular Toxicology*, 22(4): 268-273, 2008.
Luke et al., "Role of vascular congestion in cisplatin-induced acute renal failure in the rat", *Nephrology Dialysis Transplantation*, 7: 1-7, 1992.
Pabla and Dong, "Cisplatin nephrotoxicity: mechanism and renoprotective strategies", *Kidney International*, 73: 994-1007, 2008.
Ries and Klastersky, "Nephrotoxicity induced by cancer chemotherapy with special emphasis on cisplatin toxicity", *American Journal of Kidney Diseases*, 5: 368-379, 1986.
Wang and Lippard, "Cellular processing of platinum anticancer drugs", 4: 307-320, 2005.
Yokozawa et al , "Inhibition of nitric oxide release by an aqueous extract of *Tinospora tuberculata*", *Phytotherapy research*, 14: 51-53, 2000.

*Primary Examiner* — Qiuwen Mi
(74) *Attorney, Agent, or Firm* — Parker Highlander PLLC (57) ABSTRACT

Disclosed is a composition including an *Elsholtziae Herba* extract as an active ingredient, which can be used for the prevention, improvement, or treatment of acute renal failure.

5 Claims, 6 Drawing Sheets

COMPOSITION COMPRISING NATURAL SUBSTANCE EXTRACT AS ACTIVE INGREDIENT FOR PREVENTING OR TREATING ACUTE RENAL FAILURE

The present application is a national phase application under 35 U.S.C. §371 of International Application No. PCT/KR2013/010017, filed Nov. 6, 2013, which claims benefit of priority to Korean Application No. 10-2012-0126354, filed Nov. 8, 2012, the entire contents of each of the applications being hereby incorporated by reference.

BACKGROUND OF THE INVENTION

1. Field of the Invention

The present invention relates to a pharmaceutical composition or a health functional food composition including an *Elsholtziae Herba* extract as an active ingredient for the prevention, improvement, or treatment of acute renal failure.

2. Description of the Related Art

Acute renal failure is a clinical syndrome characterized by rapid decline in renal functions, which is caused by a number of factors such as a reduction in renal blood flow, glomerulonephritis, use of nephrotoxic antibiotics and anticancer agents, etc. The acute renal failure is accompanied by reductions in glomerular filtration rate (GFR) and urine output, azotemia caused by retention of nitrogenous waste products, perturbations in fluid and electrolyte balance, etc. Renal impairment in acute renal failure is associated with a high risk of 50% mortality, because it is difficult to restore the functions if the cause is not managed and thus early treatment is failed.

Particularly, azotemia, also called uremia, in acute renal failure is caused by the acute loss of renal function due to damage to renal tubules or reduction in glomerular filtration rate (GFR). A healthy adult must excrete a minimum of about 400 ml of urine each day to eliminate wastes from the body through the kidneys. Urine output less than 400 ml per day may indicate loss of kidney function, The cause of acute renal failure can be largely divided into three categories on the basis of the kidney: pre-renal acute renal failure caused by inadequate blood circulation to the kidneys, intrinsic acute renal failure caused by damage to the kidney itself, and post-renal acute renal failure caused by an obstruction which can occur at any point of the urinary tract from the renal tubules to urethra. The symptoms of acute renal failure are caused by reduced blood flow to the kidneys, such as profound dehydration, excessive bleeding, burns, severe vomiting, diarrhea, long-term use of diuretics, pancreatitis and peritonitis, sepsis, burns, increased sodium excretion by the kidney, and this status is called pre-renal acute renal failure. In addition, a direct damage to the kidney due to disease or renal toxic substance may cause changes in renal parenchyma, and this status is called intrinsic acute renal failure. Diseases corresponding to intrinsic acute renal failure include glomerulonephritis, renal vasculitis, long-lasting systemic renal failure or drug-induced acute renal tubular necrosis, thrombosis, external injury, atherosclerosis, and tumors in the kidneys.

As described above, there are many factors that cause acute renal failure. However, renal failure is caused by not one factor but complex actions or interactions between different factors. Further, acute renal failure shows a variety of physical signs. In some cases, acute renal failure has no symptom but abnormal findings in laboratory tests. The symptoms involves low urine output, but not in all cases, poor appetite, nausea and vomiting, asterixis, edema, hypertension. In advanced stages, it develops dyspnea, seizures, and coma, leading to death in the most severe case.

The pathophysiology of cisplatin-induced acute renal failure has not been fully understood yet, but it is reported that the mechanisms of anticancer drugs, together with environmental factors, are involved. Exogenous cisplatin-induced acute renal failure that accounts for most of acute renal failure is attributed to absorption of cisplatin by urinary tubular cells in the kidneys.

Recently, it was reported that efficacies of natural substance on acute renal failure can be assessed by measuring changes in ROS (Reactive Oxygen Species), GSH (Glutathione) and p53 (El-Sayed el-SM et al. 2008, Takako Yokozawa, et al 2000). In particular, it is common that levels of ROS, GSH and p53 inducing and worsening symptoms are measured in the severity test of acute renal failure.

Of them, the ROS production level is known as a biochemical index associated with renal injury in various pathological conditions, and ROS-induced DNA damage leads to p53 activation. For this reason, high levels of ROS generally indicate the presence of renal disease. Further, increased GSH content indicates a cell-protecting effect, that is, a defense effect. In cisplatin-induced acute renal failure, the levels of ROS and GSH are changed. This change has been used as a basic index for diagnosing cisplatin-induced acute renal failure.

Meanwhile, it was known that p53 expression levels are increased in cisplatin-induced acute renal failure, and p53 expression is suppressed when therapeutic effects on acute renal failure occur.

Cisplatin (cis-diaminedichloroplatinum II) used to induce acute renal failure is one of anticancer drugs frequently used, and it induces acute renal failure due to structural abnormalities of renal tubules. Free radicals are known to play an important role in cisplatin-induced renal tubule damage. Cisplatin-induced nephrotoxicity is also associated with an increase in lipid peroxidation in the kidney. It was reported that cisplatin itself prevents antioxidant effect in the kidney and reduces the level of GSH showing antioxidant effect in the kidney.

On the other hand, *Elsholtziae Herba* is prepared from the dried aerial parts of *Elsholtzia splendens* NAKAI or *E. ciliata* (THUNB.) HYLANDER, which, is a perennial herb belonging to the family Lamiaceae, and is known to have efficacies of promoting diaphoresis to eliminate summer-heat, promoting diuresis to dissipate dampness, and warming the stomach to regulate the middle, and to be used in oriental medicine for the treatment of feeling cold and chills in summer, headache and fever, chills and anhidrosis, a pain in the midriff, vomiting and diarrhoea, edema, beriberi, etc. (Young-sung Ju. Ungok Herbology (Vol. I). Seoul: Seolimje. 2004. 64-66). Of the prior studies, Korean Patent No. 10-0857691 discloses a composition including the *Elsholtziae Herba* extract for inhibiting diabetic complications, in which the *Elsholtziae Herba* extract shows excellent inhibitory effects on advanced glycosylated end products and aldose reductase, so as to be used for the prevention or treatment of diabetic complications. Further, Korean Patent Publication No. 10-2012-0032405 discloses a pharmaceutical composition including the *Elsholtziae Herba* extract as an active ingredient for the prevention or treatment of allergic diseases, in which the *Elsholtziae Herba* extract reduces histamine release from mast cells triggered by compound 48/80, generation of allergy-inducing cytokines (TNF-a, IL-4 and IL-8) increased by PMA and A23187, and edema, dermatitis and serum IgE level in an atopic dermatitis mouse model.

However, none of the above documents disclose effects of the *Elsholtziae Herba* extract on nephrotoxicity, particularly, acute renal failure.

Accordingly, the present inventors have made many efforts to develop a therapeutic agent for acute renal failure, which exhibits fewer side-effects and superior effects as a natural substance. As a result, they found that the *Elsholtziae Herba* extract exhibits the effects of inhibiting ROS generation, increasing GSH levels, and reducing p53 expression in an acute renal failure cell model and thus it can be used as a composition for the prevention and treatment of acute renal failure, thereby completing the present invention.

SUMMARY OF THE INVENTION

An object of the present invention is to provide a pharmaceutical composition for the prevention or treatment of acute renal failure, including an *Elsholtziae Herba* extract as an active ingredient.

Another object of the present invention is to provide a health functional food composition for the prevention or improvement of acute renal failure, including the *Elsholtziae Herba* extract as an active ingredient.

Still another object of the present invention is to provide a method for preventing, improving, or treating acute renal failure using the pharmaceutical composition or the health functional food composition including the *Elsholtziae Herba* extract as an active ingredient.

Still another object of the present invention is to provide a use of the *Elsholtziae Herba* extract in the preparation of the pharmaceutical composition or the health functional food composition for the prevention, improvement or treatment of acute renal failure.

DETAILED DESCRIPTION OF THE PREFERRED EMBODIMENTS

In order to achieve the above objects, the present invention provides a pharmaceutical composition including an *Elsholtziae Herba* extract as an active ingredient for the prevention or treatment of acute renal failure.

As used herein, the term "*Elsholtziae Herba*" has a scientific name of "*Elsholtzia ciliata* Hylander" and a Latin name of "*Elsholtziae Herba*", and refers to the dried aerial part of *Elsholtzia splendens* NAKAI or *E. ciliata* (THUNB.) HYLANDER, which is a perennial herb belonging to the family Lamiaceae. The *Elsholtziae Herba* has a narrow rectangular stem with long oval-egg shaped leaves being opposite pairs with finely serrated edges, and a flower stalk at the end of the stem. The stem is 20 cm to 50 cm in length, the leaf is 3 cm to 10 cm in length and 1 cm to 3 cm in width, and the spike is 3 cm to 10 cm in length and 5 mm to 10 mm in diameter. The exterior is greyish green to yellowish green, and the flower is red-purple to red-brown and has short white hairs. Traditionally, *Elsholtziae Herba* has been known to show effects of warming the stomach, harmonizing the middle, promoting diaphoresis to eliminate summer-heat, warming the stomach to regulate the middle, and promoting diuresis to dissipate dampness. It acts on the stomach and lung, and its nature is known to be non-toxic and mild.

With respect to the objects of the present invention, the *Elsholtziae Herba* is used for the prevention or treatment of acute renal failure.

The *Elsholtziae Herba* according to the present invention may be purchased from commercially available sources or collected from or cultured in the wild, but is not limited thereto.

As used herein, the term "extract" refers to a substance that is isolated and obtained from *Elsholtziae Herba*, and specifically, a substance that is isolated and obtained using a typical extraction solvent known in the art, for example, water, $C_{1-4}$ alcohol (e.g., methanol, ethanol, butanol, etc.), or a mixture of alcohol and water.

Preferably, the *Elsholtziae Herba* extract according to the present invention may be a $C_1$-$C_4$ alcohol extract, and more preferably, an ethanol extract.

In a specific embodiment, the *Elsholtziae Herba* extract was prepared by pulverizing *Elsholtziae Herba*, adding 7 L of 70% ethanol to 700 g of the pulverized product, carrying out extraction using an ultrasonic extractor for 1 hour three times, carrying out filtration to remove insoluble substances, and then concentrating the resultant at 60° C. under reduced pressure.

The *Elsholtziae Herba* extract of the present invention may also include those obtained by applying an additional purification process. For example, fractions which are obtained by various purification methods, such as those obtained by passing the *Elsholtziae Herba* extract according to the preparation method of the present invention through an ultrafiltration membrane with a predetermined molecular weight cut-off value or separating it through various chromatographic (based on size, charge, hydrophobicity or affinity) techniques are also included in the *Elsholtziae Herba* extract of the present invention.

Further, the *Elsholtziae Herba* extract of the present invention may be prepared in a powder form by additional process such, as distillation under reduced pressure, freeze-drying or hot-air drying.

As used herein, the term "acute renal failure" refers to an acute clinical syndrome characterized by rapid decline in renal functions, which is caused by a number of factors such as a reduction in renal blood flow, glomerulonephritis, use of nephrotoxic antibiotics and anticancer agents. The *Elsholtziae Herba* extract according to the present invention may be used for the prevention or treatment of the disease.

On the other hand, cisplatin is a chemotherapeutic drug for malignant tumors including many types of cancers such as testicular, head and neck, ovarian, cervical, non-small cell, or renal cancer (Pala and Dong, 2008; Wang and Lippard, 2005). However, 25~35% of cancer patients experience a significant decline in renal function after the administration of a single dose of cisplatin (Luke et al., 1992), and the most serious side effect in the renal function is a rapid decline in renal function, that is, acute renal failure (Ries and Klastersky, 1986).

As used herein, the term "prevention" refers to all of the actions by which acute renal failure is restrained or retarded by administration of the composition including the *Elsholtziae Herba* extract. As used herein, the term "treatment" refers to all of the actions by which the symptoms of acute renal failure have taken a turn for the better or been cured completely by administration of the composition including the *Elsholtziae Herba* extract.

It is common that levels of "ROS (Reactive Oxygen Species), GSH (Glutathione) and p53" inducing and worsening symptoms are measured in the severity test of acute renal failure. ROS is a biochemical index associated with renal injury in various pathological conditions, and the increased ROS level indicates a reduction in glomerular filtration rate (GFR). For this reason, high levels of ROS generally indicate the presence of renal disease. Further, GSH or p53 expression level has been used as a basic index for diagnosing acute renal failure induced by an anticancer agent such as cisplatin.

Accordingly, in an exemplary embodiment, the present inventors induced acute renal failure using cisplatin and measured the ROS, GSH and p53 expression levels in order to examine whether the *Elsholtziae Herba* extract according to the present invention shows a prophylactic or therapeutic effect on acute renal failure. As a result, remarkably increased ROS production, reduced GSH content, and increased p53 expression were observed in cisplatin-induced acute renal failure, compared to a non-treated control group. In this regard, when the *Elsholtziae Herba* extract was treated together with cisplatin, ROS production was reduced, GSH content was increased, and p53 expression was suppressed at a level similar to or better than those in the control group. Therefore, it can be seen that the composition including the *Elsholtziae Herba* extract according to the present invention as an active ingredient can be used for the prevention or treatment of acute renal failure.

Figure 2:
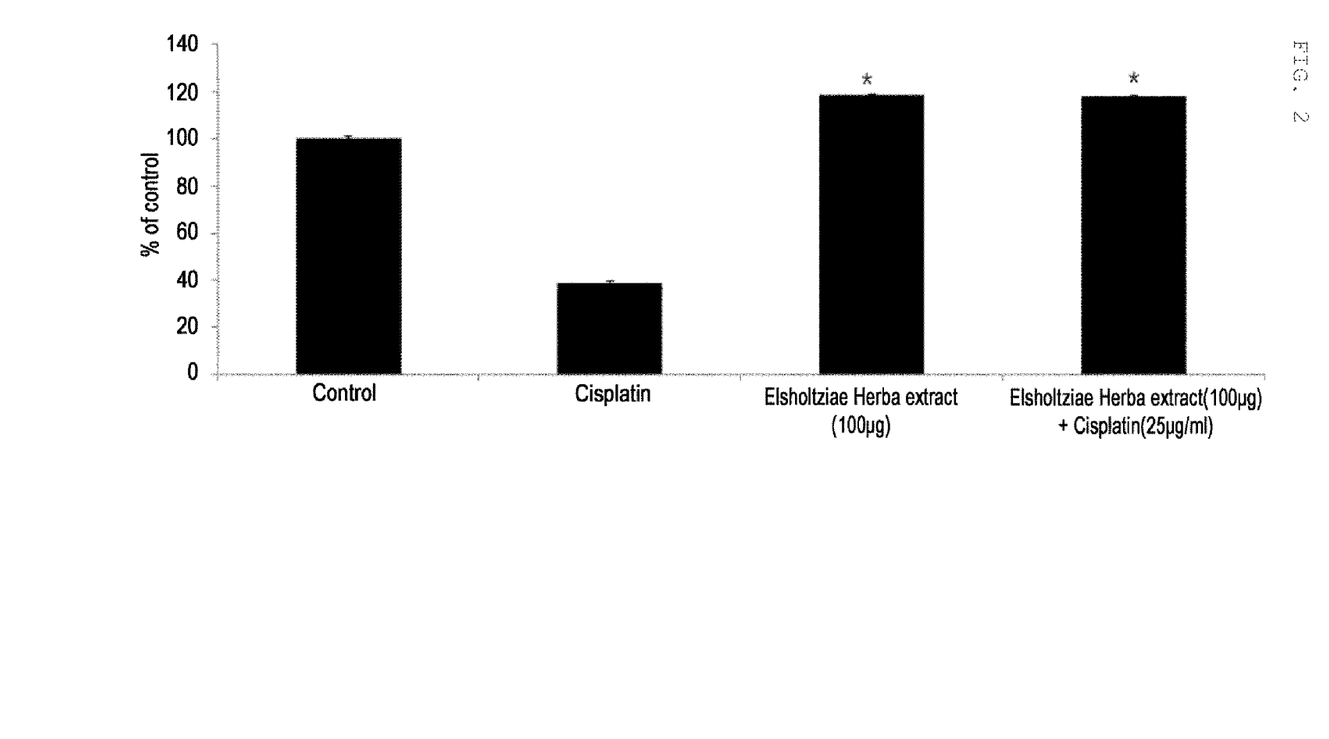
FIG. 2 is a graph showing the results of MTT assay of cisplatin- and/or *Elsholtziae Herba* extract-treated cells according to an embodiment of the present invention.

In another exemplary embodiment, treatment of renal cells with cisplatin remarkably reduced cell viability by about 40%, when cell viability of the normal control group was taken as 100%, whereas co-treatment of the *Elsholtziae Herba* extract with cisplatin showed 100% or higher cell viability, compared to the normal control group, indicating that the *Elsholtziae Herba* extract of the present invention is able to effectively protect renal cells from cisplatin cytotoxicity (FIG. 2).

In another aspect, the present invention provides a method for preventing or treating acute renal failure by administering the pharmaceutical composition including the *Elsholtziae Herba* extract as an active ingredient to a subject including human in need thereof.

As used herein, the term "subject" refers to all animals including humans who have already had acute renal failure or have a possibility of having acute renal failure. The above disease may be effectively prevented and treated by administering the composition of the present invention to the subject.

The composition of the present invention may be administered in a pharmaceutically effective amount. As used herein, the term "pharmaceutically effective amount" refers to an amount sufficient to treat diseases, at a reasonable benefit/risk ratio applicable to any medical treatment. The effective dosage level may be determined depending on a subject's type, severity of the disease, the subject's age and sex, activity of the drug, sensitivity to the drug, administration time, administration route, excretion rate, duration of treatment, drugs used in combination with the composition, and other factors known in the medical field. The composition of the present invention may be administered alone or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, this amount can be easily determined by one of ordinary skill in the art.

The preferred administration dose of the pharmaceutical composition of the present invention may be 0.1 mg/kg/day to 1,000 mg/kg/day.

The composition of the present invention may include a pharmaceutically acceptable carrier, excipient, or diluent, in addition to the *Elsholtziae Herba* extract. Examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxy benzoate, propylhydroxy benzoate, talc, magnesium stearate and mineral oil, but are not limited thereto.

According to the conventional methods, the composition of the present invention may be formulated into an oral preparation such as a powder, a granule, a tablet, a capsule, a suspension, an emulsion, a syrup, or an aerosol, an external preparation, suppository, or a sterilized injectable solution. In detail, such preparations may be prepared using commonly used diluents or excipients, such as a filler, an extender, a binder, a wetting agent, a disintegrating agent, and a surfactant. Examples of the solid preparation for oral administration include a tablet, a pill, a powder, a granule, and a capsule, but are not limited thereto. The solid preparation may be prepared by mixing with at least one excipient such as starch, calcium carbonate, sucrose, lactose, or gelatin. Further, in addition to the excipients, lubricants such as magnesium stearate and talc may be used. It may be prepared by adding various excipients, for example, a wetting agent, a sweetener, a flavor, or a preservative, in addition to a liquid for internal use and liquid paraffin. Examples of the preparation for parenteral administration include an aseptic aqueous solution, a non-aqueous solvent, a suspension, an emulsion, a lyophilized agent, and suppository. As the non-aqueous solvent and suspension, propylene glycol, polyethylene glycol, plant oil such, as olive oil, or an injectable ester such as ethyloleate may be used. As a suppository base, witepsol, macrogol, tween 61, cacao butter, lauric butter, glycerogelatin or the like may be used.

The composition of the present invention may be administered via an oral route or a parenteral route (e.g., intravenously, subcutaneously, intraperitoneally, or topically) according to the desired method, and the administration dose may be properly determined by one of ordinary skill in the art, depending on a patient's conditions and body weight, severity of the disease, type of the drug, administration route and time.

In still another aspect, the present invention provides a health functional food composition including the *Elsholtziae Herba* extract, as an active ingredient for the: prevention or improvement, of acute renal failure. The *Elsholtziae Herba* extract, and acute renal failure are the same as described above.

As used herein, the term "improvement" refers to all of the actions by which the parameters associated with conditions under treatment, for example, the symptoms are lessened.

The health functional food, may include various nutrients, vitamins, minerals (electrolyte), flavoring agents such as synthetic flavoring agents and natural flavoring agents, coloring agents and improving agents (cheese, chocolate, etc.), pectic acid and salts thereof, alginic acid and salts thereof, organic acids, protective colloidal thickening agents, pH controlling agents, stabilizing agents, preservatives, glycerin, alcohol, carbonizing agents as used in carbonated beverages, etc. Additionally, the health functional food may include fruit flesh for the preparation of natural fruit juices, fruit juice beverages and vegetable juices. These components may be used alone or in combination. In addition, the health functional food may be any one of meats, sausages, bread, chocolate, candies, snack, confectionery, pizza, noodles, gums, ice creams, soups, beverages, teas, functional water, drinks, alcoholic beverages and multivitamin preparations.

Further, the health functional food may further include a food additive, and whether or not the health functional food is suitable as a "food additive material" is determined based on a standard and criteria relating to a relevant item according to general rules disclosed in Korean Food Additives Codex and a general test method that have been approved by Korea Food & Drug Administration as long as other rules is not provided.

The items disclosed in such "Korean Food Additives Codex" may include, for example, a chemically synthetic composite, such as ketone, glycine, calcium citrate, nicotinic acid, and cinnamic acid; a natural additive material, such as persimmon color, a licorice extract, microcrystalline cellulose, and guar gum; and mixed formulations, such as sodium L-glutamate formulation, alkali agents for noodles, preservative formulation, and tar color formulation.

In the preparation of the health functional food, the content of the extract according to the present invention which is added to foods including drinks may be properly adjusted, if necessary.

In still another aspect, the present invention provides a method for preventing or improving acute renal failure comprising administering the health functional food composition to a subject.

In still another aspect, the present invention provides a use of the *Elsholtziae Herba* extract in the preparation of the pharmaceutical composition or the health functional food composition for the prevention, improvement or treatment of acute renal failure.

The pharmaceutical composition for the prevention or treatment of acute renal failure, and the health functional food composition for prevention or improvement of acute renal failure are the same as described above.

Hereinafter, the preferred Examples are provided for better understanding. However, these Examples are for illustrative purposes only, and the invention is not intended to be limited by these Examples.

EXAMPLE 1

Preparation of *Elsholtziae Herba* Extract

Commercially available *Elsholtziae Herba* was purchased and pulverized, and 7 L of 70% ethanol was added to 700 g of the pulverized product, followed by ultrasonic extraction using an ultrasonic extractor for 1 hour three times. The liquid extract was filtered using Whatman (46 cm×57 cm) filter paper to remove insoluble materials, and concentrated under reduced pressure at 60° C. using a concentrator equipped with a cooling condenser. To completely remove the solvent from the extract thus concentrated under reduced pressure, 100 mL of purified water was added and suspended, and thus 45.39 g of the extract was obtained using a freeze dryer (yield: 6.48%).

EXPERIMENTAL EXAMPLE 1

Cytotoxicity Test

In order to examine cytotoxicity of the *Elsholtziae Herba* extract prepared in Example 1, the following experiment was performed. First, porcine renal epithelial cells were seeded at a density of $1\times10^4$ cells per well of 96-well plate, and then the cells were treated with the *Elsholtziae Herba* extract prepared by the method of Example 1 at a concentration of 10, 20, 50, 100, or 200 µg/ml (treatment concentration: 20, 40, 100, 200, and 400 µg/ml). The drug treatment dose was 50 µl, and after culture for 24 hrs, final treatment was carried out at a final PBS concentration of 1% (treatment concentration: 2%), Stock: 20 mg/ml (in FES: 100 mg/ml dilution) and then absorbance at 450 nm was measured and calculated, and the mean value of wells was used. The measured values of the experimental results at respective concentrations for 24 hours were compared, and the results are shown in FIG. 1.

Figure 1:
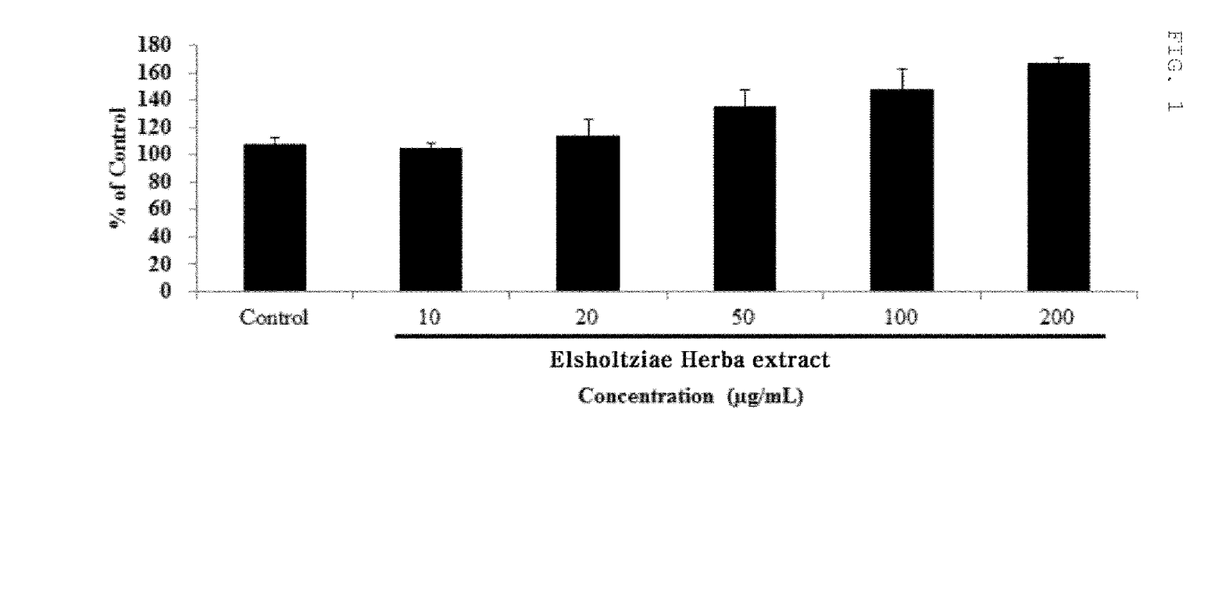
FIG. 1 is a graph showing the results of cytotoxicity test of *Elsholtziae Herba* extract according to an embodiment of the present invention.

As shown in FIG. 1, it was found that the number of cells was not reduced by treatment of the *Elsholtziae Herba* extract, indicating that the *Elsholtziae Herba* extract itself has no cytotoxicity.

EXPERIMENTAL EXAMPLE 2

In vitro Efficacy Test in Acute Renal Failure

<1> MTT assay

To measure cell viability of renal cells by the *Elsholtziae Herba* extract, MTT assay was performed. First, renal epithelial cells were seeded at a density of $1\times10^4$ cells per well of 96-well plate. After 24 hours, the cells were treated with each 50 µg thereof which was prepared by dilution at three final concentrations (50, 100, and 200 µg/ml). After 2 hours, cisplatin was treated at a final concentration of 25 µg/ml, and cells were cultured for 24 hours. After 24 hours, 10 µl of the assay reagent of EZ-Cytox Cell Viability assay kit was added to each well using a Micro multi Pipette, taking care to introduce no bubbles, and reaction was allowed, for 4 hours under basic culture conditions. Absorbance at 450 nm was measured. p<0.005 was considered statistically significant.

As shown in FIG. 2, it was found that single treatment of the *Elsholtziae Herba* extract showed 100% cell viability or higher, when cell viability of the control group was taken as 100%, indicating that the *Elsholtziae Herba* extract does not affect cell viability, In contrast, it was found that single treatment of cisplatin showed about 40% cell viability or less, indicating its cytotoxicity. In this regard, co-treatment of cisplatin with the *Elsholtziae Herba* extract showed excellent cell viability being identical or similar to that of the control group or single treatment of the *Elsholtziae Herba* extract.

Figure 3:
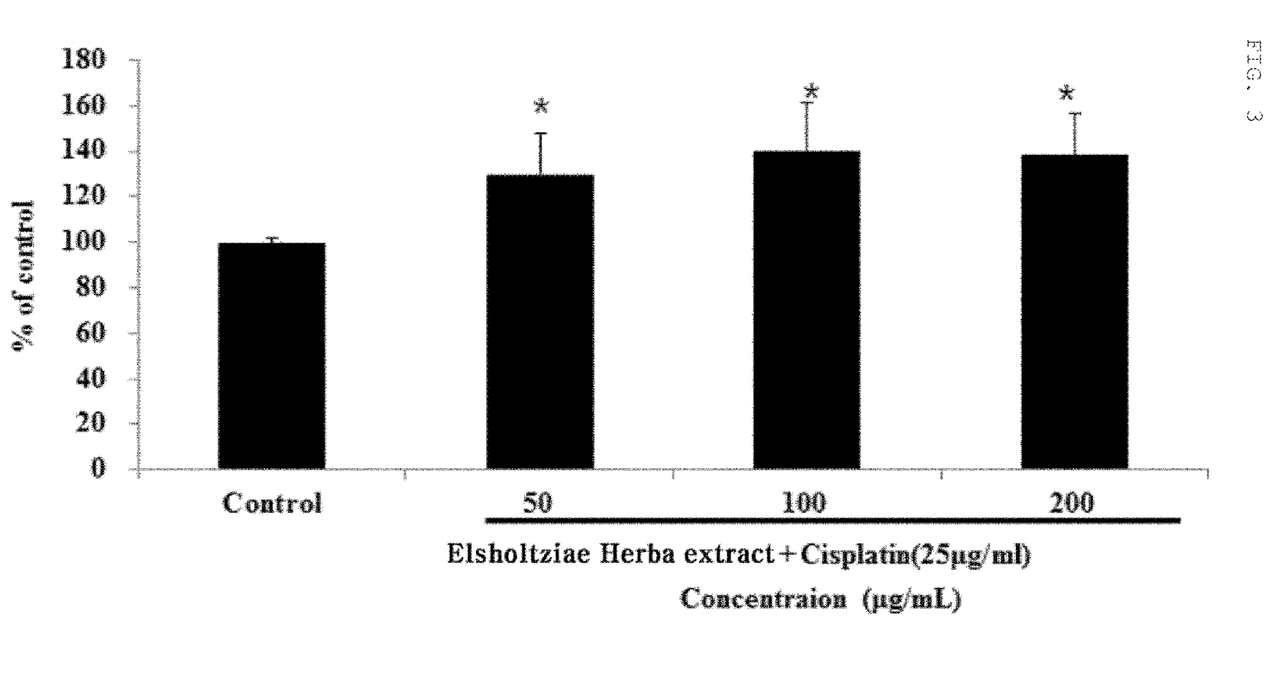
FIG. 3 is a graph showing the results of comparing cell viability between a control group and *Elsholtziae Herba* extract and cisplatin-treated cells according to an embodiment of the present invention.

As shown in FIG. 3, when cisplatin was treated together with the *Elsholtziae Herba* extract at different concentrations, excellent cell viability was observed by the concentration of 200 µg/ml showing no cytotoxicity, as confirmed in Experimental Example 1.

<2> Measurement of ROS Generation

In order to measure antioxidant effect of the *Elsholtziae Herba* extract in renal cells, ROS generation test was performed. First, renal epithelial cells were seeded at a density of $1 \times 10^5$ cells per well of 96-well plate. After 24 hours, the cells were pre-treated with 100 µg of the *Elsholtziae Herba* extract. 2 hours after treatment, cisplatin was treated at a final concentration of 25 µg/ml, followed by culture for 24 hours. DCF-DA dissolved in PBS was treated in the dark according to the treatment concentration of DCF-DA and the reaction time which were determined by historical data and preliminary experiment, and reaction was allowed for 5 hours under basic culture conditions. At the time point of 0, 4, 8, 12, 16, 20, 24 hr, end-point fluorescence wavelength at Ex: 485 nm and Em: 528 nm was measured at S=50.

Figure 4:
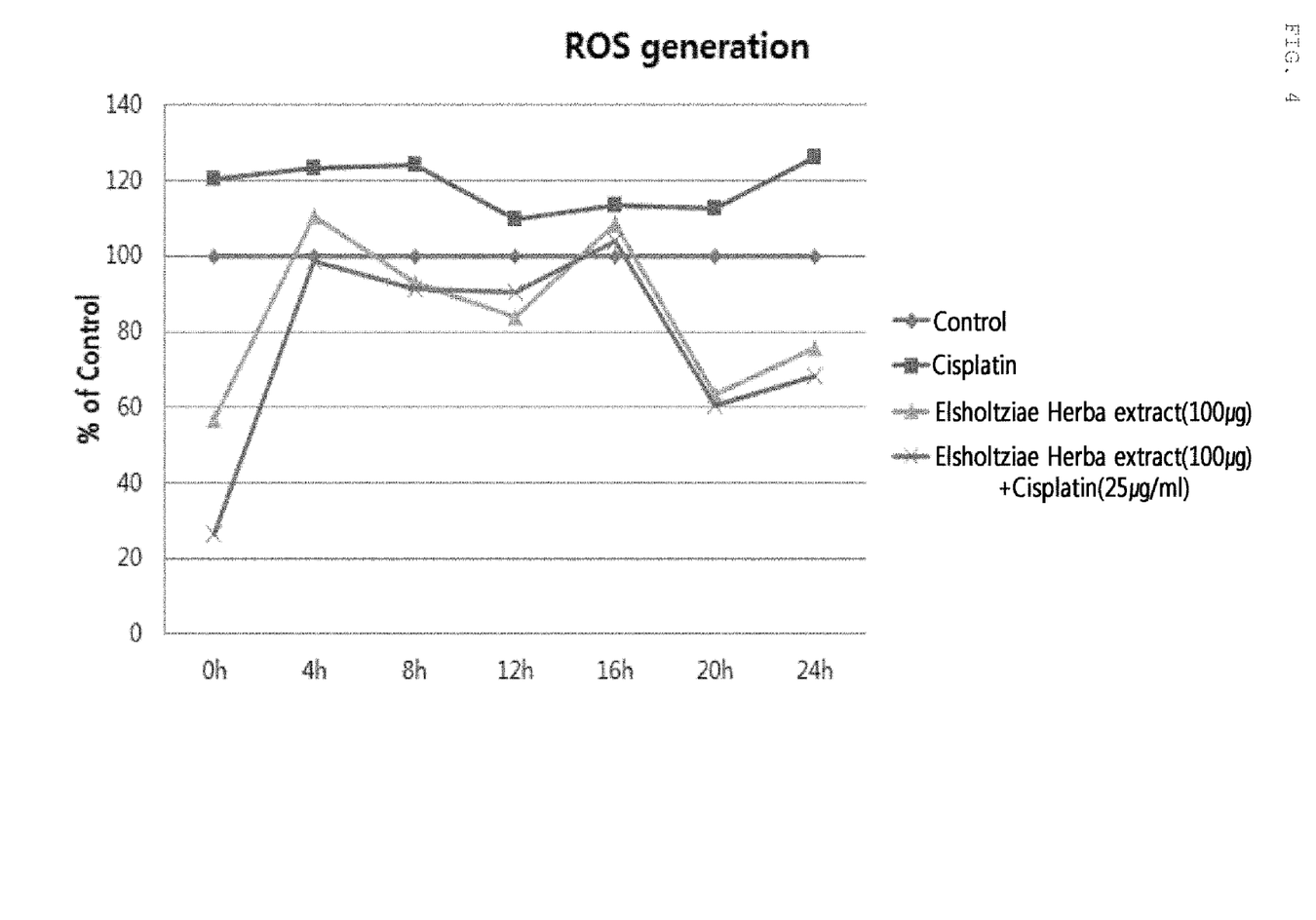
FIG. 4 is a graph showing the results of measuring the antioxidant activity index, ROS generation in cisplatin- and/or *Elsholtziae Herba* extract-treated cells according to an embodiment of the present invention.

As shown in FIG. 4, single treatment of *Elsholtziae Herba* extract showed about 75% ROS generation after 24 hours, when ROS generation of the control group was taken as 100%, indicating that the *Elsholtziae Herba* extract effectively reduces ROS generation. In contrast, single treatment of cisplatin showed about 125% ROS generation or higher after 24 hours, indicating remarkable nephrotoxicity. In this regard, co-treatment of cisplatin with the *Elsholtziae Herba* extract showed a reduction in ROS generation, which was identical to or better than that, of single treatment of the *Elsholtziae Herba* extract.

Therefore, it can be seen that single treatment of *Elsholtziae Herba* extract shows inhibitory effects on ROS generation in renal cells, that is, a renal cell protecting effect, and when a nephrotoxic agent such as cisplatin is treated together with the *Elsholtziae Herba* extract, cisplatin-induced ROS generation can be remarkably reduced to effectively inhibit nephrotoxicity.

<3> Measurement of GSH Content

Because GSH level is known as an index to evaluate a cell-protecting effect on drug-induced cellular injury, GSH level was measured to examine the cell-protecting effect of the *Elsholtziae Herba* extract against cisplatin. Monochlorobimane was employed to determine the GSH levels, and experiments for measuring GSH content were performed using the kidney tissues with reference to the conventional method of Fernandez-Checa and Kaplowitz. The number of cells, in which GSH is detectable, was determined by historical data and preliminary experiment, and $2 \times 10^6$ cells were seeded to each well of culture plate. After culture for 24 hours, the dilution fold of the final concentration of the drug determined as an active drug was considered and calculated, based on the results of MTT Assay and crystal violet Assay. The drug was diluted and pre-treated, and cisplatin was added at a final concentration of 25 µg/ml at 2 hours after drug treatment, followed by culture for 24 hours. Cells were harvested using 0.25% Trypsin-EDTA, and then centrifuged at 1,200 rpm for 3 minutes. Cold buffer was added to the resulting cell pellet, followed by sonication for 30 seconds. Centrifugation was carried out at 10,000 rpm for 15 minutes, and then the supernatant was collected and used for BCA protein quantification. 1 g/ml of MPA diluted in D.W was added to the supernatant at a volume ratio of 4:1, followed by immediately vortexing. Centrifugation was carried out at 10,000 rpm for 15 minutes, and the deprotenized supernatant was collected and prepared as a sample for GSH assay. The remainder was stored at $-20°$ C. For measurement, first, GSH Standard (L-Glutathione reduced, Sigma-Aldrich) was diluted in D.W at a concentration of 0, 0.2, 0.4, 0.8, 1.2, 1.6, and 2.0 µg/ml, and repeated twice or more times, and then each 20 µl thereof was added to renal epithelial cells in 96-well black plates. The same amount of the sample was added repeatedly twice or more times, and then 180 µl of buffer was added to each well. 10 µl of OPA (Phthaldialdehyde, Sigma-Aldrich) which was diluted in anhydrous methanol at a concentration of 1 mg/ml was added to each well, and allowed to react at room temperature for 15 minutes. End-point fluorescence wavelength at Ex: 360 nm and Em: 460 nm was measured at S=70. Data of the experimental results were analyzed using a Microsoft Excel program, and post-test analysis using Bonferroni multiple comparison test was performed to investigate the differences between the groups. $p<0.001$ was considered statistically significant.

Figure 5:
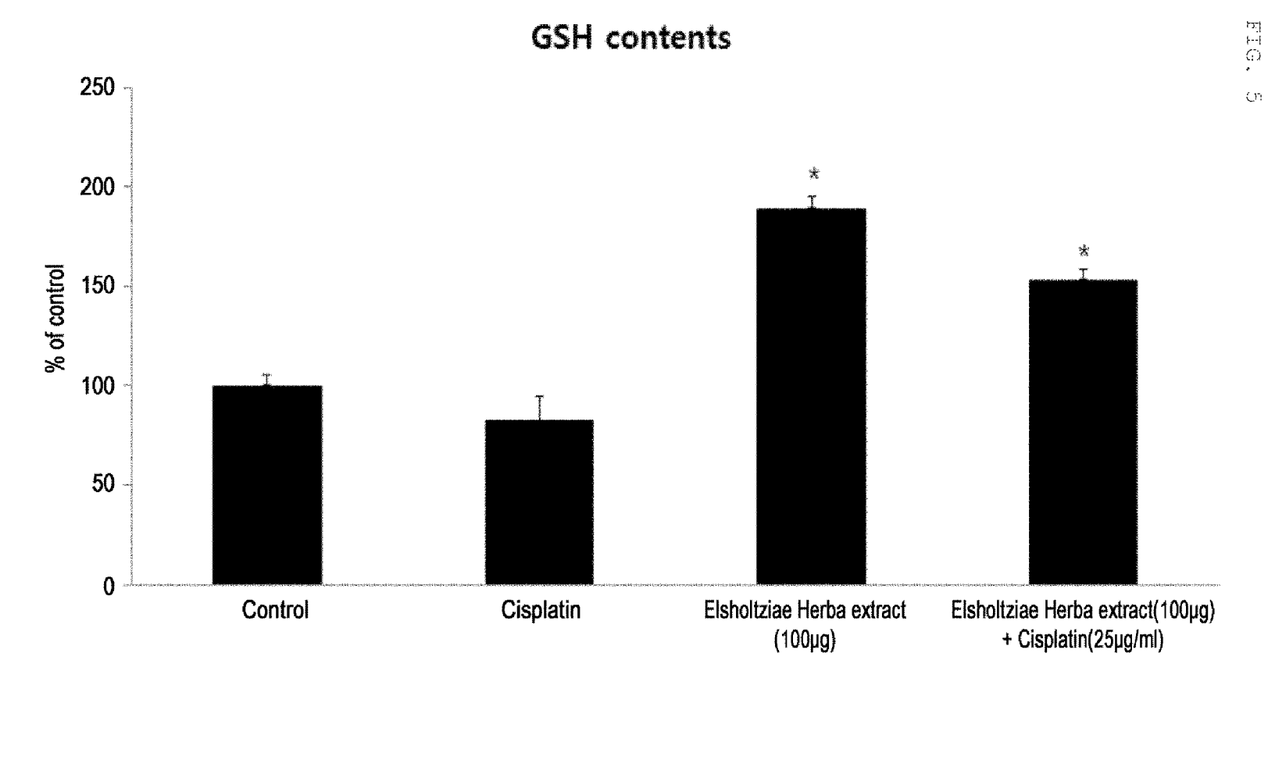
FIG. 5 is a graph showing the: results of measuring the GSH content, which indicates a cell-protecting effect on cell injury of cisplatin- and/or *Elsholtziae Herba* extract-treated cells according to an embodiment of the present invention.

As shown in FIG. 5, the GSH content was reduced by single treatment of cisplatin, but recovered at the level higher than that of the normal control group by co-treatment of cisplatin with the *Elsholtziae Herba* extract. Therefore, it can be seen that the *Elsholtziae Herba* extract effectively restores cisplatin-induced cell injury and has excellent cell-protecting effects.

<4> Examination of p53 Expression Pattern

Cells treated with *Elsholtziae Herba* extract and/or cisplatin were harvested, and RIPA buffer was added thereto, followed by sonication for cell lysis. Centrifugation was performed at 15,000 rpm for 15 minutes, and the supernatant was obtained, and subjected to protein quantification by BCA assay. The protein was loaded at an amount of 20 µg/10 µl in each well, and 12% SDS-PAGE polyacrylamide gel electrophoresis was performed, and transferred to a nitrocellulose membrane. The membrane was blocked with 5% Skim milk-TBST, and then treated with primary antibody (anti-p53/dilution—1:300). p53 was detected with HRP conjugated anti-mouse IgG (dilution—1:5000) and immune reaction was visualized by ECL. The measurement results are shown as Mean±S.E.M. (standard error of mean) in FIG. 6. Data of the experimental results were analyzed using a Microsoft Excel program, and post-test analysis using Bonferroni multiple comparison test was performed to investigate the differences between the groups. $p<0.001$ was considered statistically significant, and expressed as *; $p<0.001$ to compare with cisplatin.

Figure 6:
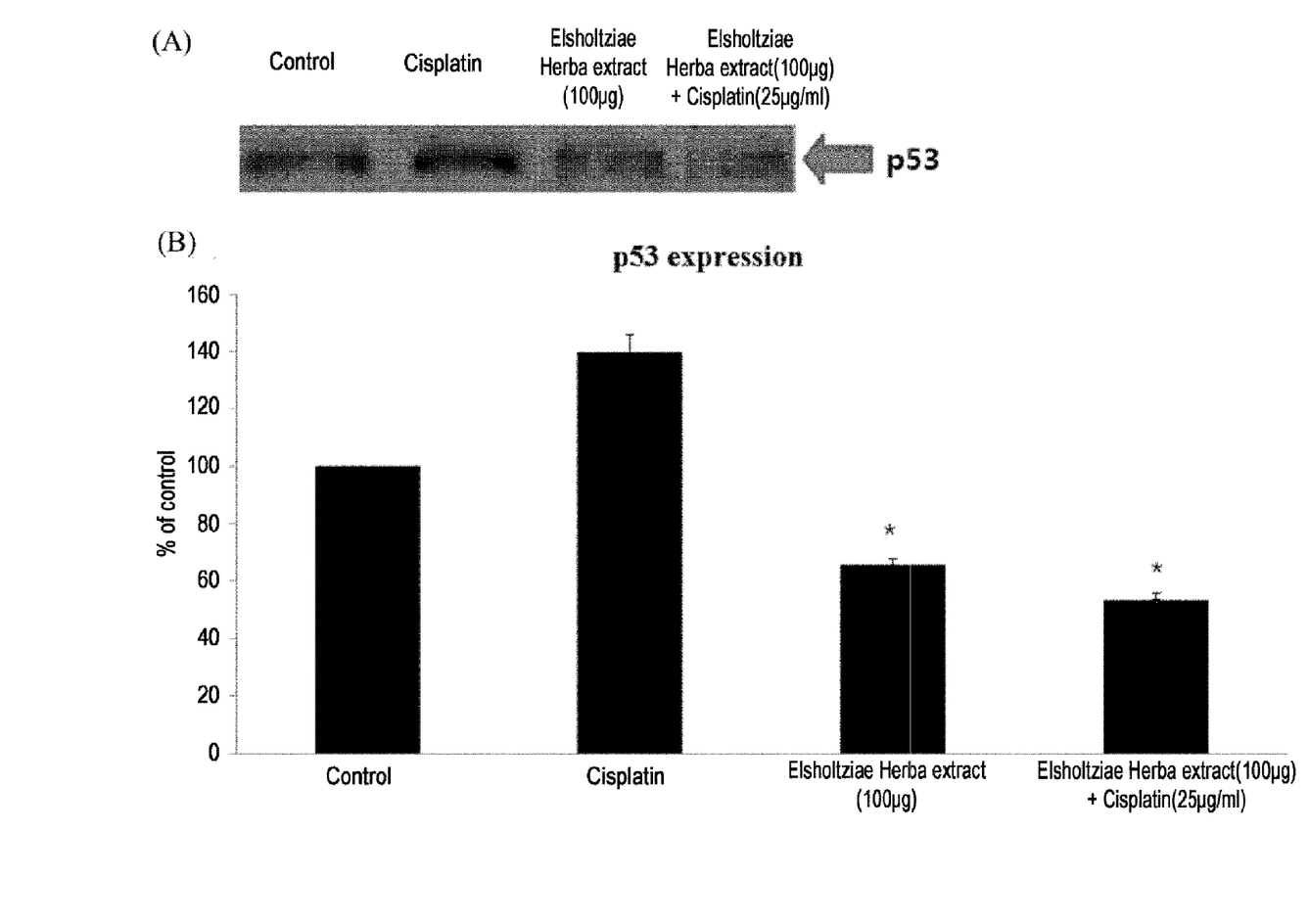
FIG. 6 is the result of electrophoresis (A) and a graph (B) thereof showing the results of measuring p53 expression pattern, which indicates cell death of cisplatin- and/or *Elsholtziae Herba* extract-treated cells according to an embodiment of the present invention.

As shown in FIG. 6, the p53 expression level was remarkably increased by single treatment of cisplatin, whereas the p53 expression level by the co-treatment of cisplatin with the *Elsholtziae Herba* extract was lower than that of the normal control group.

EFFECT OF THE INVENTION

The *Elsholtziae Herba* extract according to the present invention exhibits the effects of reducing ROS generation, increasing GSH content, and reducing p53 expression in an acute renal failure cell model, and therefore, it can be used as a composition for the prevention and treatment of acute renal failure.

What is claimed is:

1. A method for the treatment of acute renal failure, comprising administering an effective amount of a composition comprising an *Elsholtziae Herba* extract as an active ingredient to a subject in need thereof wherein the acute renal failure is caused by a renal toxic substance.

2. The method of claim 1, wherein the renal toxic substance is an anticancer agent.

3. The method of claim 2, wherein the anticancer agent is cisplatin.

4. The method of claim 1, wherein the *Elsholtziae Herba* extract is prepared by extracting *Elsholtziae Herba* using water, $C_1$-$C_4$ alcohol or a mixture thereof.

5. The method of claim 1, wherein the *Elsholtziae Herba* extract is prepared by extracting *Elsholtziae Herba* with ethanol.

* * * * *